United States Patent
Ning et al.

(10) Patent No.: US 10,729,736 B2
(45) Date of Patent: Aug. 4, 2020

(54) COMPOSITION FOR REDUCING BLOOD LIPID AND USE THEREOF AS HEALTHCARE DIETARY SUPPLEMENTS

(71) Applicant: Infinitus (China) Company Ltd., Jiangmen (CN)

(72) Inventors: Jialing Ning, Guangzhou (CN); Yiting Yang, Guangzhou (CN); Zehua Chen, Guangzhou (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 221 days.

(21) Appl. No.: 14/615,437

(22) Filed: Feb. 6, 2015

(65) Prior Publication Data
US 2016/0038554 A1 Feb. 11, 2016

(30) Foreign Application Priority Data
Aug. 11, 2014 (CN) .......................... 2014 1 0392792

(51) Int. Cl.
| | |
|---|---|
| *A61K 36/00* | (2006.01) |
| *A61K 36/55* | (2006.01) |
| *A61K 35/60* | (2006.01) |
| *A61K 31/575* | (2006.01) |
| *A61K 31/202* | (2006.01) |
| *A23L 33/11* | (2016.01) |
| *A23L 33/115* | (2016.01) |

(52) U.S. Cl.
CPC ............. *A61K 36/55* (2013.01); *A23L 33/11* (2016.08); *A23L 33/115* (2016.08); *A61K 31/202* (2013.01); *A61K 31/575* (2013.01); *A61K 35/60* (2013.01); *A23V 2002/00* (2013.01)

(58) Field of Classification Search
CPC ....................................................... A61K 36/00
USPC ........................................................ 424/725
See application file for complete search history.

(56) References Cited

FOREIGN PATENT DOCUMENTS

FR 2943506 * 10/2010

OTHER PUBLICATIONS

BG Healthwatch, 2017, 7 pages.*

* cited by examiner

*Primary Examiner* — Michael V Meller
(74) *Attorney, Agent, or Firm* — Yue (Robert) Xu; Apex Attorneys at Law, LLP

(57) ABSTRACT

The present invention discloses a blood lipid-reducing composition, the active components of the composition are composed of fish oil, linseed oil, phytosterol ester or phytosterol. The composition mainly comprises components such as α-linolenic acid, EPA, DHA and phytosterol or phytosterol ester, can reduce serum total cholesterol (TC), triglyceride (TG) and low-density lipoprotein cholesterol (LDL-C), has an efficacy of reducing blood lipid. The present invention also discloses the use of the blood lipid-reducing composition in the manufacture of health food having a function of reducing blood lipid.

2 Claims, No Drawings

COMPOSITION FOR REDUCING BLOOD LIPID AND USE THEREOF AS HEALTHCARE DIETARY SUPPLEMENTS

FIELD OF THE INVENTION

The present invention relates to the field of health food, specifically relating to a blood lipid-reducing composition and its use in the manufacture of health food having a function of reducing blood lipid.

BACKGROUND OF THE INVENTION

According to epidemiological survey, the incidence of high blood lipid in China is not less than 7%, currently there are about 90 million hyperlipidemia patients in China, of which about 36 million patients are taking lipid-reducing medicines, and about 460,000 of coronary heart disease patients need treatment of controlling blood lipid, and hyperlipidemia population has a tendency of becoming younger. Lipid-reducing medicines are different from health products in that, the former focuses on treatment, mainly targeting for the population already suffering from high lipid disease, to reduce their blood lipid level; the latter focuses on prevention, mainly targeting for those who have a tendency of high lipid to prevent the occurrence of high blood lipid, as a precaution of disease, and be of aid to reduce the blood lipid level of population who already have high blood lipid. Since health product has a safety higher than that of medicine, and it can regulate the function of human body, it is more in favor of consumers.

SUMMARY OF THE INVENTION

One purpose of the present invention is to provide a composition having a function of reducing blood lipid, the composition mainly comprises Ω-3 polyunsaturated fatty acid, phytosterol ester and phytosterols, is able to reduce the serum level of total cholesterol (TC), triglyceride (TG), low-density lipoprotein cholesterol (LDL-C), has an efficacy of reducing blood lipid.

Another purpose of the present invention is to provide the use of aforesaid composition in the manufacture of health food having a function of reducing blood lipid.

The blood lipid-reducing composition provided by the present invention, its active components are composed of fish oil, linseed oil and phytosterol ester or phytosterol.

In the composition of the present invention, fish oil is rich in Ω-3 polyunsaturated fatty acids such as EPA and DHA, it carries out the effect of regulating blood lipid mainly in a manner of reducing triglyceride (TG) in the blood, and increasing high-density lipoprotein cholesterol (HDL-C); in the meantime, fish oil has the efficacies of inhibiting inflammation, inhibiting platelet aggregation, reducing blood viscosity, thus has a function of protecting cardiovascular health; the linseed oil of plant origin is rich in α-linolenic acid, α-linolenic acid can be converted to EPA, DHA in the body, in the meantime, α-linolenic acid can reduce low-density lipoprotein cholesterol (LDL-C) in the serum; phytosterol ester or phytosterol inhibits the absorption of cholesterol by human intestine through competition so as to achieve the efficacies of reducing blood lipid, especially total cholesterol (TC) in the serum. From the aforesaid theoretical analysis, the present invention creatively administrates fish oil, linseed oil and phytosterol ester or phytosterol in combination, as proved by pharmacodynamic experiments, the aforesaid combination of these three items has a thorough and collaborative effect of reducing blood lipid.

In the composition of the present invention, the ratio of mass proportion of each component is: 1-99 parts of fish oil, 1-99 parts of linseed oil, 1-99 parts of phytosterol ester or phytosterol, these three items are mixed homogenously to be available.

In the composition of the present invention, the preferable ratio of mass proportion of each component is: 10-90 parts of fish oil, 2-20 parts of linseed oil, 1-10 parts of phytosterol ester or phytosterol.

In the composition of the present invention, the content of α-linolenic acid by weight is 0.5-50%, the content of EPA by weight is 1-75%, the content of DHA by weight is 1-55%, the content of phytosterol ester and phytosterol in total by weight is 0.5-70%.

Furthermore, the present invention provides the use of aforesaid composition in the manufacture of health food having a function of reducing blood lipid. By supplementing the blood lipid-reducing composition of the present invention, with pharmaceutically acceptable supplements, in a conventional preparation process, the health food having a function of reducing blood lipid can be manufactured, the dosage form of health food is soft capsule, soft sweet, emulsion, powder or hard capsule etc, preferably soft capsule, soft sweet or emulsion.

The blood lipid-reducing composition provided by the present invention is rich in three Ω-3 polyunsaturated fatty acids: α-linolenic acid, EPA and DHA. EPA and DHA can reduce triglyceride (TG) level, increase high-density lipoprotein cholesterol (HDL-C) level, and produce anti-inflammatory factor etc; α-linolenic acid can reduce low-density lipoprotein cholesterol (LDL-C) level, and inhibit the production of pro-inflammatory factor while producing anti-inflammatory factor; phytosterol ester or phytosterol reduces plasma cholesterol (TC) level by reducing the absorption of cholesterol, the combination of these three items achieves a thorough and collaborative effect of reducing blood lipid from different routes. The health food having a function of reducing blood lipid can be manufactured by supplementing the blood lipid-reducing composition provided by the present invention, with pharmaceutically acceptable supplements, in a conventional preparation process, thus is convenient for routine administration.

The present invention will be further demonstrated by specific embodiments and pharmacodynamic study results as follows.

SPECIFIC EMBODIMENTS

Some of the specific examples are listed as follows to demonstrate the present invention, it is necessary to point out that the following specific examples are only for further demonstrating the present invention, it is not deemed as restricting the protection scope of the present invention. The non-substantial modification or adjustment made by the others according to the present invention still fall into the protection scope of the present invention.

Example 1

5 g of fish oil, 10 g of linseed oil, 1 g of phytosterol ester or phytosterol are taken, after appropriate amount of antioxidant is added, mix homogenously to obtain blood lipid-reducing composition.

Example 2

20 g of fish oil, 20 g of linseed oil, 5 g of phytosterol ester or phytosterol are taken, after appropriate amount of antioxidant is added, mix homogenously to obtain blood lipid-reducing composition.

Example 3

25 g of fish oil, 15 g of linseed oil, 2 g of phytosterol ester or phytosterol are taken, after appropriate amount of antioxidant is added, mix homogenously to obtain blood lipid-reducing composition.

Example 4

45 g of fish oil, 25 g of linseed oil, 4 g of phytosterol ester or phytosterol are taken, after appropriate amount of antioxidant is added, mix homogenously to obtain blood lipid-reducing composition.

Example 5

50 g of fish oil, 15 g of linseed oil, 5 g of phytosterol ester or phytosterol are taken, after appropriate amount of antioxidant is added, mix homogenously to obtain blood lipid-reducing composition.

Example 6

85 g of fish oil, 20 g of linseed oil, 5 g of phytosterol ester or phytosterol are taken, after appropriate amount of antioxidant is added, mix homogenously to obtain blood lipid-reducing composition.

Example 7

60 g of fish oil, 10 g of linseed oil, 2 g of phytosterol ester or phytosterol are taken, after appropriate amount of antioxidant is added, mix homogenously to obtain blood lipid-reducing composition.

Example 8

95 g of fish oil, 2 g of linseed oil, 10 g of phytosterol ester or phytosterol are taken, after appropriate amount of antioxidant is added, mix homogenously to obtain blood lipid-reducing composition.

By supplementing the mixture prepared by aforesaid Examples 1-8, with pharmaceutically acceptable supplements, in a conventional preparation process, the health food e.g., soft capsule, soft sweet or emulsion, having a function of reducing blood lipid can be manufactured.

EPharmacodynamic Study

1. Experimental Unit

State Key Laboratory of Resource and Chemistry of Chinese Traditional Medicine, Hubei 2. Experimental Purpose To study the collaborative enhancing effect of the blood lipid-reducing composition of the present invention.

3. Experimental Materials, Grouping, Dosage and Administration Method 3.1 Experimental Material (1) The soft capsule product prepared by aforesaid Example 6, is termed as "fish oil product"; fish oil is commercially available from Novosana (Taicang) Co., Ltd./EPAX (manufacturer); linseed oil is commercially available from Honsea Sunshine Biotech Co., Ltd./sanmark (manufacturer); phytosterol ester is commercially available from Danisco (China) Co. Ltd., Fish oil product, fish oil and linseed oil are ultrasonically dissolved in 0.5% Tween-80, phytosterol ester is dissolved in 0.5% carboxymethyl cellulose sodium.

(2) Experimental animals: SD rats, male, clean level, body weight (180±20) g, provided by Laboratory Animal Center of Huhan University, License No.: SCXK(E)2008-0004.

(3) Major instruments and reagents

Roche Automatic Biochemical Analyzer, Eppendorf 5424R high-speed refrigerated centrifuge (German), JA2003-Type electronic balance, electronic scale.

Each of TC (total cholesterol), TG (total triglyceride), HDL-C (high-density lipoprotein cholesterol), LDL-C (low-density lipoprotein cholesterol) test kit is manufactured by NanJing JianCheng Bioengineering Institute, with batch No.s of 20130927, 20130914, 20130918, 20130906.

3.2 Experimental Grouping, Administration Dosage and Administration Method (1) Normal control group and High lipid control group: Intragastric administration of the same volume of 0.5% Tween-80 to test rats;

(2) Fish oil product test group (low): Intragastric administration of 0.083 g/kg.d of fish oil product solution to rats;

(3) Fish oil product test group (middle): Intragastric administration of 0.167 g/kg.d of fish oil product solution to rats;

(4) Fish oil product test group (high): Intragastric administration of 0.333 g/kg.d of fish oil product solution to rats;

(5) Fish oil group: Intragastric administration of 0.167 g/kg.d of fish oil solution to rat;

(6) Linseed oil group: Intragastric administration of 0.167 g/kg.d of linseed oil solution to rats;

(7) Phytosterol ester group: Intragastric administration of 0.167 g/kg.d of phytosterol ester solution to rats.

4. Data Processing

Data is processed by using SPSS19.0 software, one-way ANOVA is used to carry on mean comparison.

5. Experimental Content and Result 5.1 The Effect of Experimental Processing on the Body Weights of Rats It is seen from Table 1 that, 12 days after modeling, the body weights of the rats, in comparison with blank control group, have no significant difference. 35 days after administration, in comparison with model group, the body weights of rats in the fish oil product high-dosage group are significantly lower than those of model control group ($P<0.05$); the body weights of rats in the middle, low-dosage groups, in comparison with model control group, have no significant difference but are reduced, thus demonstrates that fish oil product has a certain effect of reducing body weight.

TABLE 1

The effect of experimental processing on the body weights of rats

| Groups | body weight before administration | body weight 35 days after administration |
|---|---|---|
| Normal control group | 312.87 ± 15.46 | 469.63 ± 23.35[#] |
| Model control group | 311.38 ± 18.40 | 502.00 ± 34.81 |
| Fish oil product (low) group | 316.08 ± 15.41 | 487.70 ± 35.88 |
| Fish oil product (middle) group | 310.15 ± 17.97 | 479.89 ± 38.86 |
| Fish oil product (high) group | 312.10 ± 12.97 | 471.33 ± 17.21[#] |
| Fish oil group | 314.72 ± 20.42 | 471.00 ± 38.77[#] |
| Linseed oil group | 311.09 ± 15.64 | 472.27 ± 31.32[#] |
| Phytosterol ester group | 308.90 ± 13.98 | 468.09 ± 33.12[#] |

Note:
in comparison with blank group, * $P < 0.05$, ** $P < 0.01$;
in comparison with model group, [#]$P < 0.05$, [##]$P < 0.01$, [###]$P < 0.001$ 5.2 the Effect of Experimental Processing on the Blood Lipid Profile of Rats It is seen from Table 2 that, the serum TC, TG of rats of three fish oil product dosage groups are significantly or extremely significantly lower than those of model group ($P<0.05$ or $P<0.01$), the HDL level of high-dosage group is significantly higher than that of model group ($P<0.05$), the LDL level of high-dosage group is extremely significantly lower than that of model group ($P<0.01$). With regards to fish oil group, its TG level is extremely significantly lower than that of model group ($P<0.01$), its HDL-C level is extremely significantly increased ($P<0.01$), but its effect on TC level is less than the effect in three dosage (i.e., low, middle, high) groups of fish oil product; merely the TG level of phytosterol ester group is lower than that of model group ($P<0.05$); each of the TC, TG level of linseed oil group is significantly or extremely significantly lower than that of model group ($P<0.05$ or $P<0.01$), but the LDL-C level is higher than that of model group, without a descending tendency, the LDL-C level of each fish oil product c has a descending tendency in comparison with model group, and the LDL-C level of fish oil product high-dosage group is extremely significantly lower than that of model group ($P<0.01$). Thus, the blood lipid-reducing efficacy of fish oil product group is better than those of fish oil group, linseed oil group and phytosterol ester group. The comparison result of fish oil product with every other medicine with respect to each indicator are shown in Table 2.

TABLE 2

The effect of experimental processing on the serum biochemical indicators of rats (Unit: mmol/L)

| Groups | TC | TG | HDL-C | LDL-C |
|---|---|---|---|---|
| Normal control group | 2.01 ± 0.24 | 1.78 ± 0.56 | 0.77 ± 0.12 | 0.15 ± 0.05 |
| Model control group | 2.39 ± 0.21** | 3.06 ± 0.77** | 0.59 ± 0.08** | 0.23 ± 0.07** |
| Fish oil product (low) group | 2.08 ± 0.24[##] | 2.42 ± 0.58[#] | 0.60 ± 0.09[YY] | 0.21 ± 0.06 |
| Fish oil product (middle) group | 2.11 ± 0.21[#] | 2.36 ± 0.73[#] | 0.64 ± 0.11[Y] | 0.22 ± 0.05 |
| Fish oil product (high) group | 1.83 ± 0.28[###zzYY] | 2.21 ± 0.73[##] | 0.71 ± 0.14[#] | 0.16 ± 0.05[##YYYMM] |
| Fish oil group | 2.17 ± 0.25 | 2.28 ± 0.58[##] | 0.78 ± 0.16[##] | 0.25 ± 0.03 |
| Linseed oil group | 2.06 ± 0.26[##] | 2.34 ± 0.66[#] | 0.69 ± 0.14 | 0.24 ± 0.05 |
| Phytosterol ester group | 2.18 ± 0.35 | 2.56 ± 0.62[#] | 0.66 ± 0.14 | 0.21 ± 0.04 |

Note:
in comparison with blank group, *$P < 0.05$, $P < 0.01$, *$P < 0.001$;
in comparison with model group, [#]$P < 0.05$, [##]$P < 0.01$, [###]$P < 0.001$
in comparison with fish oil group, [Y]$P < 0.05$, [YY]$P < 0.01$, [YYY]$P < 0.001$
in comparison with linseed oil group, [M]$P < 0.05$, [MM]$P < 0.01$, [MMM]$P < 0.001$
in comparison with phytosterol ester group, [z]$P < 0.01$, [zz]$P < 0.01$, [zzz]$P < 0.001$ 6. Conclusion of Experiments Each fish oil product dosage group in comparison with model control group, can reduce the contents of serum TC and TG in rats, each of the difference has significance; and high-dosage group can significantly increase the content of serum HDL-C and reduce the content of LDL-C. According to the determination standard of "The Functional Assessment Program of Health Food" issued by Ministry of Health, it is determined that fish oil soft capsule product has an efficacy of aiding for reducing the blood lipid of complex-type hyperlipidemia rat.

In a single raw material group, with respect to fish oil group, its TG level is extremely significantly lower than that of model group ($P<0.01$), its HDL-C level is extremely significantly increased ($P<0.01$), but its effect on TC level is less than the effect in three dosage (i.e., low, middle, high) groups of fish oil product; merely the TG level of phytosterol ester group is lower than that of model group ($P<0.05$); each of the TC, TG level of linseed oil group is significantly or extremely significantly lower than that of model group ($P<0.05$ or $P<0.01$), but the LDL-C level is higher than that of model group, without a descending tendency, the LDL-C level of each fish oil product group has a descending tendency in comparison with model group, and the LDL-C level of fish oil product high-dosage group is extremely significantly lower than that of model group ($P<0.01$). Thus, the efficacy of fish oil product groups for aiding for reducing blood lipid is better than single administration of fish oil, linseed oil and phytosterol ester, which indicates that fish oil product formula has an enhancing effect in the aspect of reducing blood lipid.

What is claimed is:

1. A capsule consisting essentially of 85 parts by weight of fish oil, 20 parts by weight of linseed oil, and 5 parts by weight of phytosterol ester.

2. A capsule consisting essentially of 85 parts by weight of fish oil, 20 parts by weight of linseed oil, and 5 parts by weight of phytosterol.

* * * * *